(12) United States Patent
Dzakula et al.

(10) Patent No.: US 8,241,246 B2
(45) Date of Patent: Aug. 14, 2012

(54) SIDE BY SIDE LUMEN CATHETER AND METHOD OF MANUFACTURE THEREOF

(75) Inventors: Zdravka Dzakula, Bachenbuelach (CH); Malinee Buchmeier, Neuhausen (CH)

(73) Assignee: Abbott Laboratories Vascular Enterprises Ltd., Dublin (IE)

( * ) Notice: Subject to any disclaimer, the term of this patent is extended or adjusted under 35 U.S.C. 154(b) by 486 days.

(21) Appl. No.: 11/752,232

(22) Filed: May 22, 2007

(65) Prior Publication Data

US 2007/0276325 A1 Nov. 29, 2007

Related U.S. Application Data

(60) Provisional application No. 60/802,337, filed on May 22, 2006.

(51) Int. Cl.
*A61M 29/00* (2006.01)
(52) U.S. Cl. ........................ 604/96.01; 604/40
(58) Field of Classification Search ............... 604/40, 604/96.01
See application file for complete search history.

(56) References Cited

U.S. PATENT DOCUMENTS

| | | | |
|---|---|---|---|
| 4,782,834 A | 11/1988 | Maguire et al. | |
| 5,085,636 A * | 2/1992 | Burns | 604/99.04 |
| 5,217,482 A * | 6/1993 | Keith | 606/194 |
| 5,261,879 A | 11/1993 | Brill | |
| 5,370,655 A | 12/1994 | Burns | |
| 5,413,559 A | 5/1995 | Sirhan et al. | |
| 5,423,754 A | 6/1995 | Cornelius et al. | |
| 5,480,383 A * | 1/1996 | Bagaoisan et al. | 604/102.02 |
| 5,498,240 A | 3/1996 | Bagaoisan et al. | |
| 5,538,510 A * | 7/1996 | Fontirroche et al. | 604/265 |
| 5,549,552 A * | 8/1996 | Peters et al. | 604/103.1 |
| 5,569,201 A * | 10/1996 | Burns | 604/102.02 |
| 5,649,909 A | 7/1997 | Cornelius | |
| 5,879,324 A | 3/1999 | von Hoffmann | |
| 6,027,475 A | 2/2000 | Sirhan et al. | |
| 6,068,634 A * | 5/2000 | Lorentzen Cornelius et al. | 623/1.11 |
| 6,227,093 B1 | 5/2001 | Rensky, Jr. | |
| 6,893,417 B2 | 5/2005 | Gribbons et al. | |
| 7,575,568 B2 * | 8/2009 | Holman et al. | 604/96.01 |
| 2002/0165571 A1 * | 11/2002 | Hebert et al. | 606/192 |
| 2003/0032920 A1 * | 2/2003 | Wantink | 604/103 |
| 2003/0149465 A1 * | 8/2003 | Heidner et al. | 623/1.11 |
| 2004/0197601 A1 * | 10/2004 | Thompson et al. | 428/690 |
| 2005/0015135 A1 * | 1/2005 | Shanley | 623/1.11 |
| 2005/0038467 A1 * | 2/2005 | Hebert et al. | 606/194 |
| 2005/0059991 A1 * | 3/2005 | Shanley | 606/192 |
| 2005/0060885 A1 * | 3/2005 | Johnson et al. | 29/846 |
| 2005/0167032 A1 * | 8/2005 | Lumauig | 156/158 |
| 2005/0267408 A1 | 12/2005 | Grandt et al. | |
| 2007/0043324 A1 * | 2/2007 | Shibata et al. | 604/192 |

* cited by examiner

*Primary Examiner* — Nicholas Lucchesi
*Assistant Examiner* — Gerald Landry, II
(74) *Attorney, Agent, or Firm* — Fulwider Patton LLP

(57) ABSTRACT

The present invention provides a dual lumen catheter shaft having a first dual lumen section and a second dual lumen section with a transition section therebetween. The present invention further provides a method of forming a dual lumen catheter shaft.

9 Claims, 2 Drawing Sheets

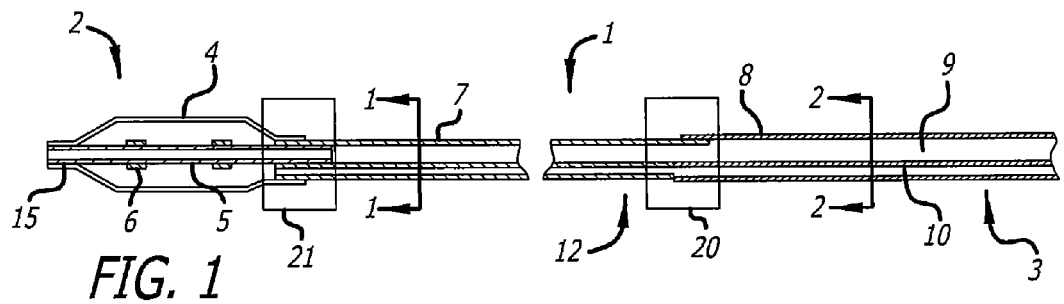
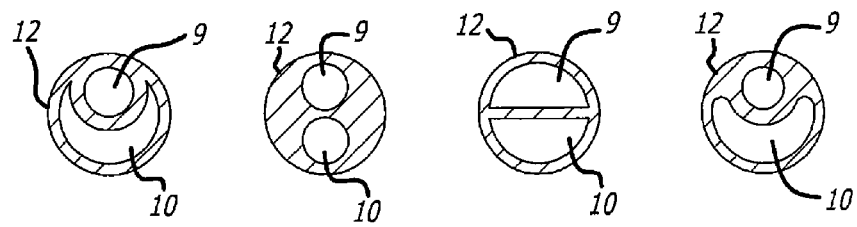
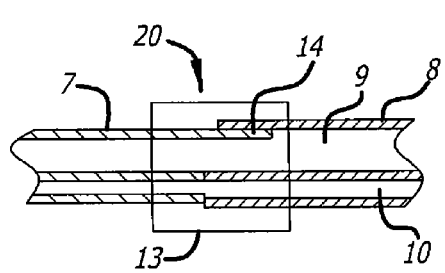
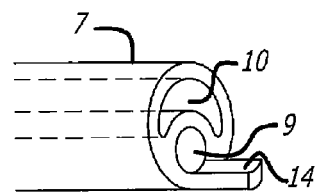
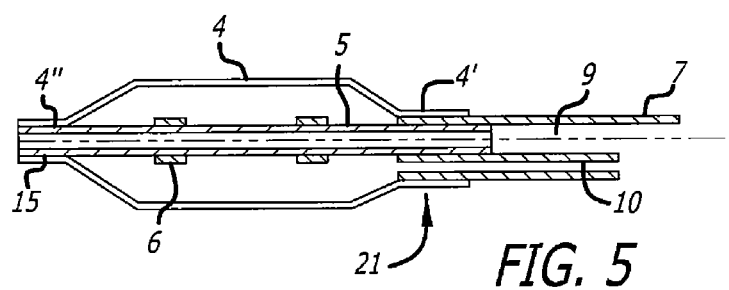

SIDE BY SIDE LUMEN CATHETER AND METHOD OF MANUFACTURE THEREOF

CROSS-REFERENCE TO RELATED APPLICATIONS

This application claims the benefit of U.S. Provisional Patent Application No. 60/802,337, filed May 22, 2006, the entire disclosure of which is incorporated herein by reference.

FIELD OF THE INVENTION

The present invention relates to a catheter for POBA or stent delivery applications. More specifically, the invention relates to a catheter having variable stiffness along the length of the catheter and a method to produce such a catheter.

BACKGROUND OF THE INVENTION

Non-invasive procedures such as percutaneous transluminal angioplasty (PTA), percutaneous transluminal coronary angioplasty (PTCA), stent delivery and deployment, radiation treatment, delivery of a drug at a lesion site and other procedures are used in the treatment of intravascular disease. These therapies are well known in the art and usually utilize a balloon catheter disposed over a guide wire. After a guiding catheter is placed into the patient's main vessel, a guide wire is advanced in the guide catheter and beyond the distal end of the guide catheter. The balloon catheter is then advanced over the guidewire until it reaches the treatment site at the lesion or stenosis. The balloon is inflated to compress the lesion site and dilate the previous narrowed lesion or stenosis site. If the balloon carried a stent and/or drug, the stent and/or drug is delivered at the site when the balloon is inflated. Likewise, further therapies may also use a balloon catheter for the treatment of the lesion site.

Catheters used in vascular procedures must be flexible and soft to navigate safely through tortuous anatomy of the patient's vessels without damaging the vessels, but at the same time they need sufficient stiffness to allow for good pushability and traceability of the catheter. As a result, catheters have been designed to have a more flexible distal end and a stiffer proximal portion. For example, each of U.S. Pat. No. 4,782,834 to Maguire and U.S. Pat. No. 5,370,655 to Burns discloses a catheter having sections along its length, which are formed from materials having a different stiffness. U.S. Pat. No. 5,423,754 to Cornelius discloses a catheter having a greater flexibility at its distal portion due to both a material and dimensional transition in the shaft; and U.S. Pat. No. 5,649,909 to Cornelius discloses a catheter having a proximal portion with greater stiffness due to a change from a dual lumen tube to two separate tubes running in parallel to each other or the second tube being coiled around the first tube.

However, there continues to be a need for a catheter with a flexible distal section of the catheter and a stiffer proximal section that allows the catheter to follow the tortuous path to a vessel lesion providing enough trackability and pushability. In particular, there continues to be a need for a simple and effective method of producing such a catheter. The present invention addresses this need by providing a dual lumen catheter and a novel way to produce such a catheter.

SUMMARY OF THE INVENTION

To achieve these and other objects, there is provided a dilation balloon in accordance with the present invention. The dilatation balloon catheter according to the present invention is an OTW (Over-The-Wire) balloon catheter comprising a dual lumen shaft. The catheter includes an elongated shaft with a first and a second longitudinally extending luminal opening positioned side by side therein, an inflatable balloon sealed about the shaft near the distal end of the shaft in fluid communication with the first luminal opening. The shaft has a proximal portion, a middle portion and a distal portion and transition sections in between, wherein the distal portion has smaller dimensions than the middle portion and the middle portion has smaller dimensions than the proximal portion.

In accordance with the present invention there is provided a method of forming a dual lumen shaft comprising a first dual lumen section and a second dual lumen section and a transition section in between.

In further accordance with the present invention, a catheter tip configuration is provided that provides a smooth transition between the catheter tip and a guidewire disposed therein.

BRIEF DESCRIPTION OF THE DRAWINGS

For a further appreciation of the above and other advantages, reference is made to the following detailed description and to the drawings, in which:

FIG. 1 is a schematic sectional view of an exemplary embodiment of the dilation balloon catheter in accordance with the present invention;

FIGS. 2A, 2B, 2C, and 2D are schematic sectional views of an embodiment of the dilatation balloon catheter in accordance with the present invention, taken along line 1-1 or line 2-2 of FIG. 1;

FIG. 3 is a schematic sectional view of a transition section of an exemplary embodiment of the dilatation balloon catheter in accordance with the present invention;

FIG. 4 is a schematic view of a distal end of a second shaft section of an exemplary embodiment of the dilatation balloon catheter in accordance with the present invention; and FIG. 5 is a schematic view of the distal part of an exemplary embodiment of the dilatation balloon catheter in accordance with the present invention;

DETAILED DESCRIPTION OF THE PREFERRED EMBODIMENTS

Figure 6:
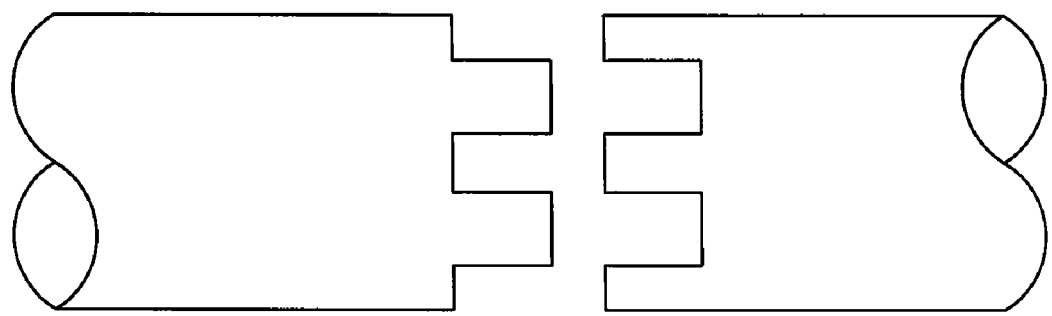
FIG. 6 is a plan view in cross-section of an alternative embodiment of a transition section of the dilatation balloon catheter in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

In accordance with the present invention there is provided a medical device, wherein the medical device includes an elongated shaft member having a proximal end and a distal end. An expandable member being disposed adjacent the distal end and in fluid communication with a lumen extending through the elongated shaft member.

In accordance with one embodiment of the present invention there is provided a balloon catheter having an elongated shaft comprising a first dual lumen shaft section and a second dual lumen shaft section and a transition section in between, wherein a first shaft section comprises a nose extending from the end of the first shaft section into the lumen of the second shaft section.

In accordance with another embodiment of the present invention, there is also provided a balloon catheter comprising an elongated shaft having a proximal dual lumen shaft section and a distal dual lumen shaft section and a transition section in between, wherein the distal shaft section comprises a nose extending from the proximal end of the distal shaft section into the distal part of a lumen of the proximal shaft section.

Further, there is provided a balloon catheter comprising an elongated shaft having a proximal dual lumen shaft section and a distal dual lumen shaft section and a transition section in between, wherein the proximal shaft section has a larger outer diameter than the distal shaft section, and wherein the distal shaft section comprises a nose extending from the proximal end of the distal shaft section into the distal part of a lumen of the proximal shaft section.

Moreover, according to the present invention there is provided a balloon catheter as depicted above that further comprises a thin tubular member disposed about and supporting the transition section.

In accordance with the present invention there is further provided a method to provide an elongated shaft having a first dual lumen shaft section and a second dual lumen shaft section and a transition section in between, comprising the steps of providing a first dual lumen shaft section and a second dual lumen shaft section comprising a nose at one end; feeding the nose of the second shaft portion into a lumen of the first shaft section thereby placing the two tubes in a manner to each other, that their ends abut each other; and bonding the shaft portions end to end.

In a further embodiment according to the present invention, a thin tubular member is disposed on the transition section before bonding is performed. Bonding can be done by thermal bonding, laser bonding, white light bonding, RF welding, or by adhesive bonding.

Referring now to FIG. 1, there is shown an expandable medical device 1 in accordance with the present invention. The medical device 1 in accordance with the present invention includes a catheter shaft 12 having a proximal end 3 and a distal end 2. The shaft 12 further comprises a guide wire lumen 9 extending between the proximal end 3 and the distal end 2 of the shaft 12. A balloon 4 is disposed adjacent the distal end 2 of the shaft. The catheter shaft further includes an inflation lumen 10 disposed therein, wherein the inflation lumen 10 is in fluid communication with an interior of the balloon 4 and the proximal end 3 of the shaft 12. The shaft 12 further includes a hub 11 (not shown) disposed on the proximal end 3, wherein the hub 11 includes two lumens, one in communication with the guide wire lumen 10 and the second in communication with the inflation lumen 9. Also, the shaft 12 further includes a tip 15 disposed at the distal end 2 of the shaft 12.

In an exemplary embodiment of the present invention, the shaft is formed of multiple portions, wherein the multiple portions are joined together to form a single unitary shaft as described herein. The shaft 12 has a first distal portion 5 bearing markers 6 and carrying the balloon, a second middle portion 7 proximal of the first distal portion 5, and a third proximal portion 8 disposed proximal of the second middle portion 7, wherein at least the second middle portion 7 and the third proximal portion 8 of the shaft 12 are preferably embodied as a dual lumen shaft. The dual lumen shaft includes the guide wire lumen 9 and the inflation lumen 10 in a side-by-side configuration. FIGS. 2A, 2B, 2C, and 2D illustrate possible cross sectional views taken along line 1-1 or 2-2 of FIG. 1. The inflation lumen 9 and guide wire lumen 10 can be arranged in any manner and are shown arranged in a parallel manner.

The proximal end of the first distal portion 5 of the catheter shaft is secured to the distal end of the second middle portion 7 of the catheter shaft at a first joint or transition section 21 formed by suitable means such as heat or laser fusion.

The proximal end of the second middle portion 7 of the catheter shaft and the distal end of the third proximal portion 8 of the catheter shaft are also secured together at a second joint or transition section 20 formed by suitable means such as heat or laser fusion as will be described in greater detail below with regard to FIG. 3.

In a preferred embodiment, the relative dimensions of the portions 5,7, and 8 of the catheter shaft 12 are selected to give enhanced performance to the shaft 12. The outer diameter of the third proximal portion 8 is preferably of a larger diameter than the outer diameter of the second middle portion 7. The different sizes of these two portions provide the catheter shaft 12 with a relatively stiff proximal portion and decreasing stiffness toward the distal portion of the shaft 12.

The decrease in outer diameter between the second middle portion 7 and the third proximal portion 8 may be less than 20%, more preferably between about 1% to 15%, more preferred between about 3% to 10%, and most preferred between about 6% to 7% compared to the larger diameter. The cross-sectional area of the inflation lumen 10 is preferred to stay approximately the same along the length of the catheter. Additionally, the diameter of the guide wire lumen 9 is preferred to stay approximately the same along the length of the catheter.

In addition to, or in combination with, that described above, the materials of the proximal portion of the catheter shaft may be selected to give enhanced performance to the shaft 12 of the catheter 1. For example, the material of which the third proximal portion 8 is constructed may be more rigid than that of the material of which the second middle portion 7 is constructed. Thus, providing the catheter shaft 12 with a relatively stiff proximal end and having decreasing stiffness toward the distal end of the shaft 12.

The catheter shaft 12 and/or the portions 5,7, and 8 that comprise the catheter shaft 12 can be constructed of materials such as Polyamides (e.g. Nylon 11, Nylon 12, Nylon 6,6, Nylon 7/11, Nylon 11/12), Polyurethanes (e.g. Tecoflex, Pellethene, Bionate, Corethane, Elasteon), Polyethylenes (e.g. PET, PBT, PVDF, ETFE, Teflon), Polyolefins (e.g. HDPE, PE, LDPE, LLDPE, polypropylene), Polyimides, Polyether-blockamides, (e.g. ELY, PEBAX), Polycarbonate blockamides (Ubesta), and blends, compositions or multilayers thereof. Further, the shaft may comprise braidings, coatings or fibers or filaments made from metal, polymers, carbon reinforced materials, boron fibers or glass fibers in order to reinforce the shaft materials. These reinforcements may be incorporated into the material of which the shaft is constructed of or be layered within the shaft construction.

Referring now to FIGS. 3 and 4, there is shown an exemplary embodiment of a transition section of the catheter 1 in accordance with the present invention. As shown in FIG. 3, the transition section 20 is formed at the junction of the second middle portion 7 and the third proximal portion 8. The transition section 20 is formed by abutting the proximal end of the second middle portion 7 against the distal end of the third proximal portion 8. As shown in FIG. 4, the second middle tube 7 further includes a protrusion 14 extending from the proximal end thereof as shown. The protrusion 14 is configured to extend into either the guide wire lumen 9 or the inflation lumen 10 of the distal end of the third proximal portion 8 as shown. In a preferred embodiment, the protrusion 14 extends into the guide wire lumen 9 of the third proximal portion 8. The protrusion 14 can be located either at the outer wall of the second middle portion 7 next to: the guide wire lumen 9, to the Inflation lumen 10, or between guide wire lumen 9 and inflation lumen 10. In a preferred embodiment, the protrusion 14 is located at the outer wall of the second middle portion 7 next to the guide wire lumen 9. Further, the protrusion 14 can be of various shapes like for example and not limitation rectangular, triangular, semicircular. Also the relative size of the protrusion 14 is variable and can be adjusted according to the need of additional material in the bonding region. In a preferred embodiment, the protrusion 14 has a length and a width each of between about 0.5 to 4 mm, more preferably between about 0.5 to 2 mm and most preferably approximately about 1 mm.

Further, a thin tubular member 13 is disposed about the portions 7 and 8 and wherein the thin tubular member is configured to support the junction 20 of the proximal and middle portions. The thin tubular member 13 may have a length of about 0.1 mm to 100 mm, preferably about 0.5 mm to 2 mm, most preferably about 1 mm. The wall thickness of the thin tubular member 13 is between 0.001 mm and 0.1 mm, preferably between 0.01 mm and 0.1 mm, most preferably approximately 0.05 mm.

The thin tubular member may be constructed of materials such as: Polyamides (e.g. Nylon 11, Nylon 12, Nylon 6,6, Nylon 7/11, Nylon 11/12), Polyurethanes (e.g. Tecoflex, Pellethene, Bionate, Corethane, Elasteon), Polyethylenes (e.g. PET, PBT, PVDF, ETFE, Teflon), Polyolefins (e.g. HDPE, PE, LDPE, LLDPE, polypropylene), Polyimides, Polyetherblockamides, (e.g. ELY, PEBAX), Polycarbonate blockamides (Ubesta), and blends, compositions or multilayers thereof.

In accordance with the present invention herein will be described an exemplary method for joining the individual sections together to form the catheter shaft 12. Referring now to FIGS. 1 and 3, in accordance with the exemplary method of the present invention, the protrusion 14 of the second middle portion 7 is disposed within the respective lumen of the third proximal portion 8 and the ends of the two portions are disposed adjacent to each other in a way that the proximal end of the second middle portion 7 abuts the distal end of the third proximal portion 8; disposing a thin tubular member 13 about the transition section 20 of the second and third shaft tube portions and bonding the shaft portions end to end by thermal bonding, laser bonding, white light bonding, RF welding, adhesive bonding or by conventional mechanical means. Further, a shrink sleeve can be placed over the transition section 20 when bonding is performed by thermal bonding, laser bonding, white light bonding, or by RF welding. It shall be further understood that mandrels may be placed within the guidewire lumen 9 and/or the inflation lumen 10 so that each of the lumens remain patent during and after the bonding process.

The protrusion 14 can be placed in any position, either at the outside of the tube next to the guide wire lumen 9 or next to the inflation lumen 10 or at the wall between the inflation lumen 10 and the guide wire lumen 9. For joining the shaft sections the protrusion 14 will accordingly be fed into the lumen located next to the protrusion. When the protrusion 14 is located at the wall in between the two lumens, both insertion into the guide wire lumen 9 and insertion into the inflation lumen 10 is possible. In a preferred embodiment, the protrusion 14 is placed at the outside of the second middle portion 7 next to the guide wire lumen 9 as depicted in FIG. 4. Accordingly, in this preferred embodiment the protrusion 14 will be fed into the guide wire lumen 9 of the third proximal portion 8.

The protrusion 14 is preferably created by cutting away a portion of the proximal end of the second middle portion 7 thereby forming the protrusion 14. It is further contemplated that more than one protrusion may be formed extending from the proximal end of the second middle portion, wherein the multiple protrusions would be utilized in the manner described above in forming the junction 20.

Referring now to FIG. 5 there is shown the transition section 21 in greater detail. As shown in FIG. 5, the first distal portion 5 of shaft 12 is preferably embodied as a generally tubular member having an outer diameter equal to or less than the diameter of the guide wire lumen of the second middle portion 7. The proximal end of the first distal portion 5 is preferably inserted into the guide wire lumen 9 of the second middle portion 7 for a short distance and bonded thereto. Additionally, the proximal balloon sleeve 4' is also disposed about the diameter of the distal end of the second middle portion 7 and bonded thereto, thereby forming the transition section 21. The distal balloon sleeve 4' is bonded to a distal end of the first shaft section 5 as shown. Bonding of each of these areas can be performed by thermal bonding, laser bonding, white light bonding, RF welding, adhesive bonding or by conventional mechanical means. As described above, shrink tubing may be placed over the proximal or distal balloon sleeves during the bonding process. Additionally, a mandrel may be inserted into the guidewire lumen 9 of each of the portions so that the lumen remains patent after bonding. A distal tip member 15 may then be disposed adjacent to and extending from the distal end of the first distal portion 5. Alternatively, the tip member 15 may be formed of the first distal portion 5, wherein a length of the distal end of the first distal portion may be reduced in diameter through known manufacturing methods to form a tip. Further still, a distal portion of the distal first member 5 may be chemically treated or altered to change the mechanical properties of the material of which the first distal member 5 is formed of, thereby forming a softened section which forms a soft distal tip 15.

Referring now to FIG. 6, there is shown an alternative embodiment of a transition section of the catheter 1 in accordance with the present invention. The transition could be at section 20 or section 21, or any other transition section in the catheter. The transition section is formed between adjacent catheter portions. Each of the catheter portion ends is shaped to mesh with the adjacent catheter portion end. For example, each catheter portion end can be shaped to include a tongue 40 and a groove 42. The tongue and groove features can be formed within the catheter portions using suitable manufacturing means such as laser cutting, micromachining, and photoetching. Further, the tongue 40 and groove 42 can be of various shapes like for example and not limitation rectangular, triangular, semicircular. Also the relative sizes of the tongue 40 and the groove 42 are variable and can be adjusted according to the need of additional material in the bonding region. In a preferred embodiment, the tongue 40 and groove 42 has a length and a width each of between about 0.5 to 4 mm, more preferably between about 0.5 to 2 mm and most preferably approximately about 1 mm.

A method for forming the transition section is also provided, which includes the steps of abutting one catheter portion end to the other catheter portion end. The ends are meshed together so that the tongues 40 and grooves 42 interconnect, forming a transition section of substantially uniform profile. A thin tubular member is disposed about the transition section of the tube portions and the shaft portions are bonded end to end by thermal bonding, laser bonding, white light bonding, RF welding, adhesive bonding or by conventional mechanical means. Further, a shrink sleeve can be placed over the transition section when bonding is performed by thermal bonding, laser bonding, white light bonding, or by RF welding. It shall be further understood that mandrels may be placed within the guidewire lumen and/or the inflation lumen so that each of the lumens remain patent during and after the bonding process.

Figure 7:
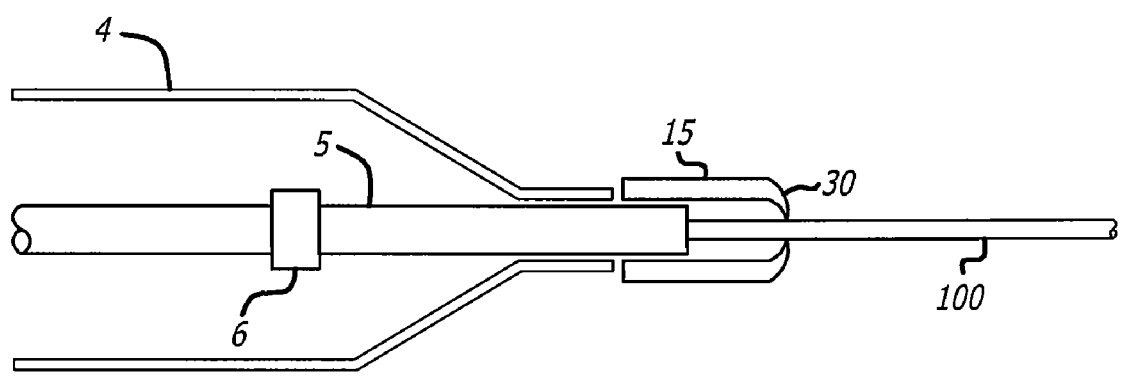
FIG. 7 is a plan view in cross-section of an alternative embodiment of a distal tip member of the dilatation balloon catheter in accordance with the present invention.

Referring now to FIG. 7, an alternative embodiment of a tip configuration is shown, in which the distal tip member 15 is disposed adjacent the distal end of the first distal portion 5. In this embodiment, the distal tip member 15 has a variable cross sectional profile in the axial direction. The inner diameter of this profile narrows toward the distal end of the distal tip member 15 forming the tip contour 30. The tip contour 30 fits closely with a guidewire 100 disposed therein, resulting in a smooth transition from the distal tip member 15 to the guidewire 100.

An additional advantage of this embodiment of the distal tip member is that the narrowing tip contour 30 may be capable of radial expansion. Therefore, it is capable of receiving guidewires of various sizes. For example, the distal end of the distal tip member 15 may be fit to receive a 0.014-inch diameter guidewire. Insertion of a 0.018-inch diameter guidewire within the distal tip member 15 will cause an interference between the guidewire and the distal tip member 15, resulting in a radial expansion of the tip contour 30. The tip contour 30 will fit closely with the guidewire disposed therein, resulting in a smooth transition from the distal tip member 15 to the guidewire. Since the inner diameter of distal tip member 15 narrows toward the distal end, only the tip contour will be interference contact with the guidewire, while the majority of the distal tip member 15 length is sized to receive a 0.018-inch guidewire. Therefore, trackability of the catheter over the guidewire will not be significantly affected by the contact between the tip contour 30 and the guidewire. In this example, the guidewire sizes are completely exemplary, and it is appreciated that the guidewires and the catheter tip can be any variety of sizes in accordance with the present invention.

Other advantages of this embodiment include the ability of the catheter to track around bends in the guidewire without the catheter tip flaring open. Since the tip contour 30 closely matches the guidewire diameter, the risk of catching the catheter tip on a vessel lesion or obstruction during tracking is reduced, as will be appreciated by those skilled in the art. In addition, this catheter tip design allows for contrast medium to be flushed through the guidewire lumen 9 of the catheter while the guidewire is in place.

While an over-the-wire (OTW) dual lumen catheter has been specifically illustrated, the present invention is not limited to an OTW dual lumen catheter, but rather equally applies to multi lumen catheters as well as rapid exchange (RX) catheters comprising a dual lumen or multi lumen portion.

It is obvious to those skilled in the art, that the method of forming the transition section 20 illustrated above can be readily applied to the formation of a joint between any single or multiple lumen portions where it is desirable to form a catheter shaft or other tubular member of more than one portions.

What is claimed is:

1. A balloon catheter having an elongated shaft comprising:
   a first shaft portion having a proximal end and a distal end and first outer diameter;
   a second shaft portion having a proximal end and a distal end and a protrusion extending from the proximal end and second outer diameter, wherein the first shaft portion is aligned longitudinally to the second shaft portion and, wherein the protrusion extends into a lumen within the first shaft portion; and
   a thin tubular sleeve-like member disposed about the first and second outer diameters of the shaft portions and about at least a part of said protrusion, thereby forming a transition section.

2. A method to provide an elongated shaft comprising a first dual lumen shaft section and a second dual lumen shaft section and a transition section in between, comprising the steps of:
   a) providing a first dual lumen shaft section and a second dual lumen shaft section having a protrusion longitudinally extending from one end;
   b) feeding the protrusion of the second shaft portion into a lumen within the first shaft section such that their ends abut each other; and
   c) bonding the shaft portions end to end.

3. A method to provide an elongated shaft comprising a first dual lumen shaft section and a second dual lumen shaft section and a transition section in between, comprising the steps of:
   a) providing a first dual lumen shaft section and a second dual lumen shaft section having a protrusion extending longitudinally from one end;
   b) feeding the protrusion of the second shaft portion into a lumen within the first shaft section to thereby cause their ends to abut one another;
   c) disposing a thin tubular member on the transition section; and
   d) bonding the shaft portions end to end.

4. A method according to claim 2, wherein the bonding is done by thermal bonding, laser bonding, white light bonding, RF welding, or by adhesive bonding.

5. A method according to claim 3, wherein the bonding is done by thermal bonding, laser bonding, white light bonding, RF welding, or by adhesive bonding.

6. The balloon catheter of claim 1, wherein the second outer diameter is less than the first outer diameter.

7. A balloon catheter, having an elongated shaft comprising:
   a first shaft portion having a proximal end and a distal end and first outer diameter;
   a second shaft portion having a proximal end and a distal end and a protrusion extending from the proximal end and second outer diameter, wherein the first shaft portion is aligned longitudinally to the second shaft portion and, wherein the protrusion extends into a lumen within the first shaft portion; and
   a thin tubular member disposed about the first and second outer diameters of the shaft portions and about at least a part of said protrusion, thereby forming a transition section, wherein both the first shaft portion and the second shaft portions have a guide wire lumen and an inflation lumen formed therein and said protrusion extends into said guide wire lumen.

8. The balloon catheter of claim 7, wherein said guide wire lumen and said inflation lumen are arranged in a side-by-side configuration.

9. A balloon catheter, having an elongated shaft comprising:
   a first shaft portion having a proximal end and a distal end and first outer diameter;
   a second shaft portion having a proximal end and a distal end and a protrusion extending from the proximal end and second outer diameter, wherein the first shaft portion is aligned longitudinally to the second shaft portion and, wherein the protrusion extends into a lumen within the first shaft portion; and
   a thin tubular member disposed about the first and second outer diameters of the shaft portions and about at least a part of said protrusion, thereby forming a transition section, wherein the protrusion has a rectangular shape.

* * * * *